(12) United States Patent
Raulerson et al.

(10) Patent No.: US 7,704,239 B2
(45) Date of Patent: Apr. 27, 2010

(54) CATHETER BUTTON HUB

(75) Inventors: J. Daniel Raulerson, Brewton, AL (US); Mark S. Fisher, Sellersville, PA (US); W. Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 1003 days.

(21) Appl. No.: 11/016,052

(22) Filed: Dec. 17, 2004

(65) Prior Publication Data

US 2005/0137580 A1 Jun. 23, 2005

Related U.S. Application Data

(60) Provisional application No. 60/531,167, filed on Dec. 19, 2003.

(51) Int. Cl.
*A61M 5/00* (2006.01)
*A61M 25/16* (2006.01)
*A61M 25/00* (2006.01)

(52) U.S. Cl. ............... 604/258; 604/533; 604/284

(58) Field of Classification Search ......... 604/533–535, 604/537, 538, 284, 7–8, 258
See application file for complete search history.

(56) References Cited

U.S. PATENT DOCUMENTS

| | | | | |
|---|---|---|---|---|
| 3,957,082 | A * | 5/1976 | Fuson et al. | 137/625.41 |
| 4,257,416 | A * | 3/1981 | Prager | 604/507 |
| 4,533,349 | A | 8/1985 | Bark | |
| D303,712 | S * | 9/1989 | Goldberg | D24/129 |
| 4,895,561 | A | 1/1990 | Mahurkar | |
| 5,061,243 | A | 10/1991 | Winchell et al. | |
| 5,135,026 | A * | 8/1992 | Manska | 137/555 |
| 5,163,926 | A | 11/1992 | Bailey et al. | |
| 5,171,216 | A | 12/1992 | Dasse et al. | |
| 5,221,256 | A * | 6/1993 | Mahurkar | 604/43 |
| 5,288,290 | A * | 2/1994 | Brody | 604/32 |
| 5,348,536 | A * | 9/1994 | Young et al. | 604/43 |
| 5,620,426 | A * | 4/1997 | Braithwaite | 604/533 |
| 5,695,478 | A * | 12/1997 | Haindl | 604/247 |
| 5,749,857 | A * | 5/1998 | Cuppy | 604/164.12 |

(Continued)

OTHER PUBLICATIONS

Supplementary European Search Report dated Dec. 28, 2007; EP Application No. 04814639.3 (3 pages).

(Continued)

*Primary Examiner*—Kevin C Sirmons
*Assistant Examiner*—Andrew M Gilbert
(74) *Attorney, Agent, or Firm*—Anton P. Ness; Fox Rothschild LLP

(57) ABSTRACT

A catheter hub (100) including a first port (104) and a second port (108) fluidly communicating with the first port through a first conduit (106). The first conduit (106) turns at an angle of greater than approximately 135 degrees between the first port (104) and the second port (108). The hub (100) also includes a third port (120) fluidly communicating with the second port (108) through a second conduit (122) that similarly turns at an angle of greater than approximately 135 degrees between the third port (120) and the second port (108). Further, the hub (100) includes a fourth port (130) fluidly communicating with the second port (108) and is generally co-axial therewith. A catheter assembly (150) that utilizes the catheter hub (100) is also disclosed.

28 Claims, 11 Drawing Sheets

U.S. PATENT DOCUMENTS

| | | | |
|---|---|---|---|
| 5,810,790 A | 9/1998 | Ebling et al. | |
| 6,206,849 B1 | 3/2001 | Martin et al. | |
| 6,641,574 B2 * | 11/2003 | Badia Segura | 604/533 |
| 6,689,096 B1 * | 2/2004 | Loubens et al. | 604/96.01 |
| 2002/0038114 A1 * | 3/2002 | Segura | 604/533 |
| 2002/0120224 A1 | 8/2002 | Zia et al. | |
| 2003/0163099 A1 * | 8/2003 | Wermeling et al. | 604/275 |
| 2005/0267445 A1 * | 12/2005 | Mendels | 604/534 |
| 2006/0089604 A1 * | 4/2006 | Guerrero | 604/247 |

OTHER PUBLICATIONS

International Search Report, PCT/US04/42486 mailed Jun. 30, 2006 (3 pages).
Written Opinion, PCT/US04/42486 mailed Jun. 30, 2006 (5 pages).
Office Action, EPA Application No. EP 04814639.3, dated Nov. 25, 2008 (5 pages).
Office Action, EP Application No. EP 04814639.3 dated Apr. 29, 2008 (6 pages).

* cited by examiner

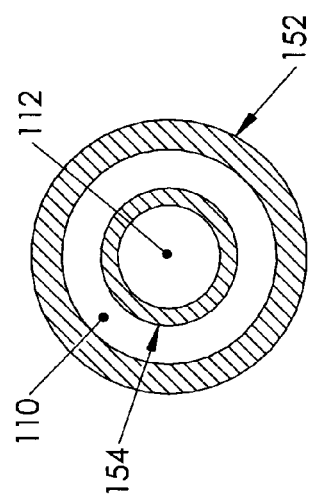
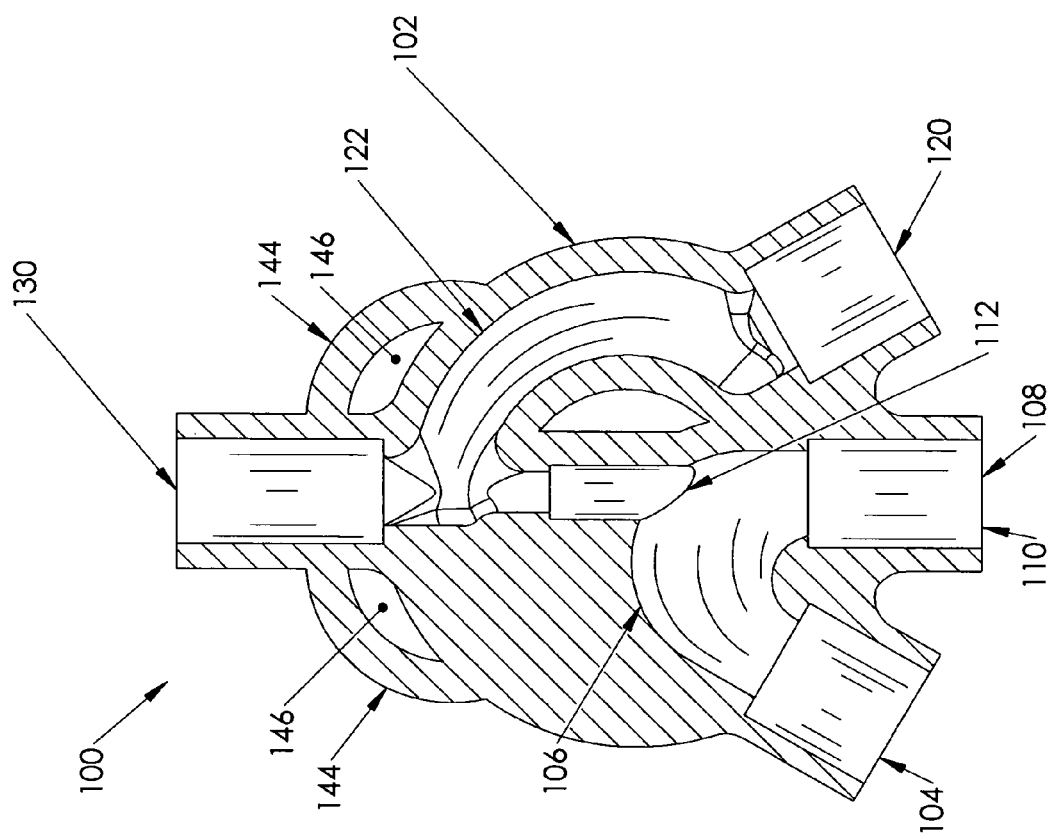

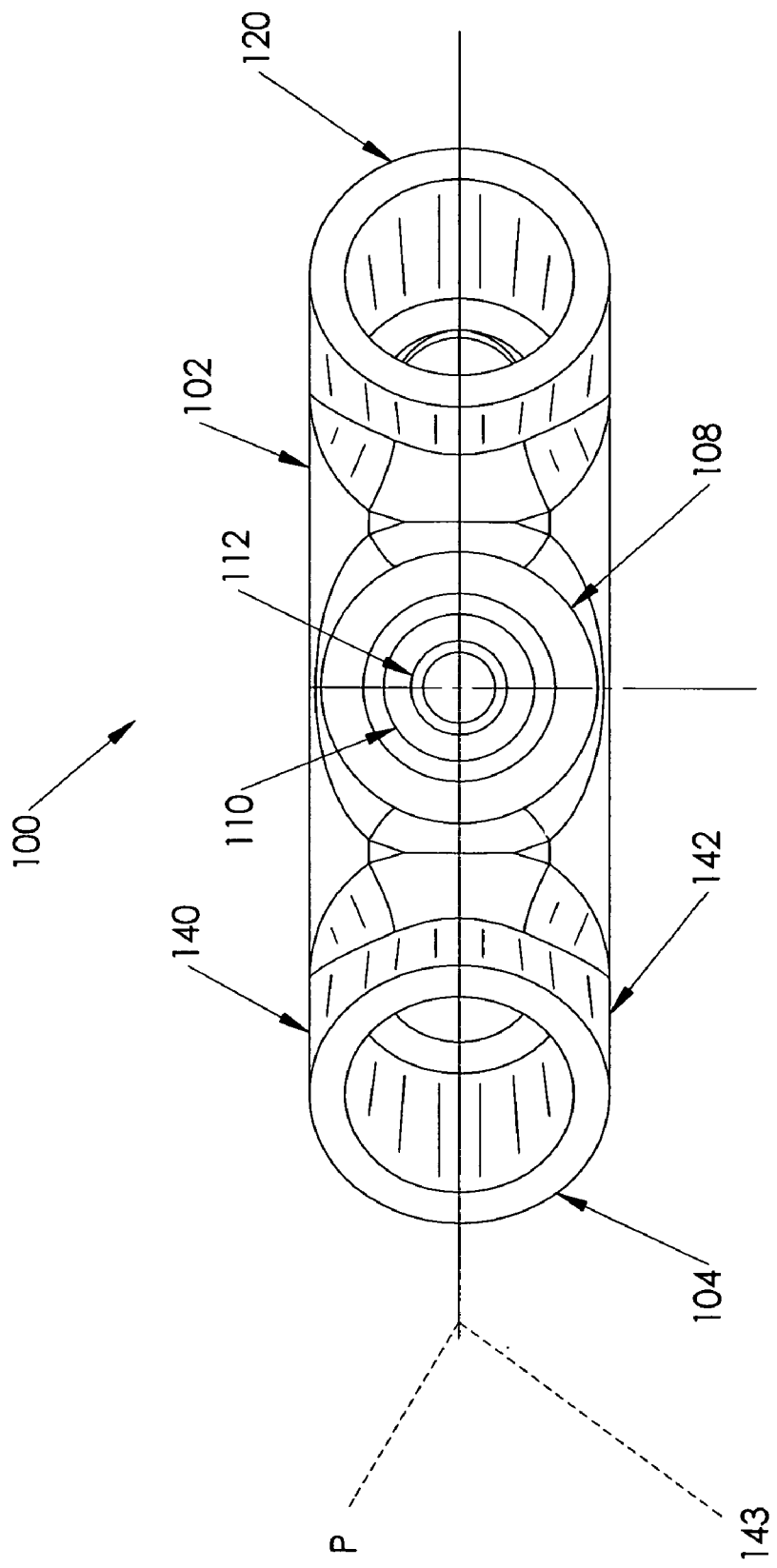

CATHETER BUTTON HUB

CROSS-REFERENCE TO RELATED APPLICATION

This patent application claims the benefit of U.S. Provisional Patent Application Ser. No. 60/531,167, filed on Dec. 19, 2003.

FIELD OF THE INVENTION

The present invention relates to a hub for a multi-lumen catheter.

BACKGROUND OF THE INVENTION

Catheters for the introduction or removal of fluids from the body of a patient may be located in various venous locations and cavities throughout the body for introduction of fluids to the body or removal of fluids from the body. Such catheterization may be performed by using multiple catheters, each with a single lumen, or by using a single catheter having multiple lumens. A typical example of a multiple lumen catheter is dual lumen catheter in which one lumen introduces fluid to the patient and the other lumen removes fluid from the patient.

Catheters may be inserted into a patient for acute care, in which the catheterization period is only a few days, or for chronic care, in which the catheterization period may extend several weeks or months. For some types of catheterization, such as in hemodialysis, the catheter is inserted into the patient's jugular vein, with a proximal portion of the catheter extending out of the patient's body proximate to the patient's neck. The connectors and clamps that make up the proximal portion of the catheter extend from the insertion site and lay near the patient's neck and facial area, tending to interfere with normal activities of the patient, particularly when the patient is moving his/her head or trying to sleep. Further, excessive movement of the proximal portion, resulting from the patient turning his/her head, may loosen or damage the catheter, which may lead to blood loss or even death.

It would be beneficial to provide a catheter in which the portion of the catheter external to the patient is disposed away from the neck and head areas of the patient.

BRIEF SUMMARY OF THE INVENTION

Briefly, the present invention provides a catheter hub comprising a first port and a second port fluidly communicating with the first port through a first conduit. The first conduit turns at an angle of greater than approximately 135 degrees between the first port and the second port. The hub also includes a third port fluidly communicating with the second port through a second conduit. The second conduit turns at an angle of greater than approximately 135 degrees between the third port and the second port. Further, the hub comprises a fourth port fluidly communicating with the second port. The fourth port and the second port are generally co-axial.

Additionally, the present invention provides a catheter assembly. The catheter assembly comprises a hub having a first port and a second port fluidly communicating with the first port through a first conduit. The first conduit turns at an angle of greater than approximately 135 degrees between the first port and the second port. The hub also includes a third port fluidly communicating with the second port through a second conduit. The second conduit turns at an angle of greater than approximately 135 degrees between the third port and the second port. The hub further includes a fourth port fluidly communicating with the second port, wherein the fourth port and the second port are generally co-axial. A first lumen fluidly communicates through the second port, to the first port, and a second lumen fluidly communicates, through the second port, to the third port and the fourth port.

Further, the present invention provides a catheter hub comprising a hub body, a first port extending from the hub body, and a second port extending from the hub body. The second port fluidly communicates with the first port through a first conduit, and the first conduit turns at an angle of greater than approximately 135 degrees between the first port and the second port. The hub further includes a third port extending from the hub body. The third port fluidly communicates with the second port through a second conduit, and the second conduit turns at an angle of greater than approximately 135 degrees between the third port and the second port. A fourth port extends from the hub body. The fourth port fluidly communicates with the second port, and the fourth port and the second port are generally co-axial. The first port, the second port, the third port, and the fourth port all lie in a plane defined by the hub body.

Also, the present invention provides a catheter hub. The catheter hub comprises a first port and a second port fluidly communicating with the first port through a first conduit. The first conduit turns at an angle of greater than approximately 135 degrees between the first port and the second port. The hub further includes a third port fluidly communicating with the second port through a second conduit. The second conduit turns at an angle of greater than approximately 135 degrees between the third port and the second port.

BRIEF DESCRIPTION OF THE DRAWINGS

The foregoing summary, as well as the following detailed description of preferred embodiments of the invention, will be better understood when read in conjunction with the appended drawings, which are incorporated herein and constitute part of this specification. For the purpose of illustrating the invention, there are shown in the drawings embodiments which are presently preferred. It should be understood, however, that the invention is not limited to the precise arrangements and instrumentalities shown. In the drawings:

FIG. 1A is an enlarged sectional view of the catheter taken along lines 1A-1A of FIG. 1.

FIG. 2 is an enlarged plan view, in section, of the catheter hub according to the first embodiment of the present invention.

FIG. 3 is an enlarged side view of the catheter hub according to the first embodiment of the present invention.

DETAILED DESCRIPTION OF THE INVENTION

Figure 1:
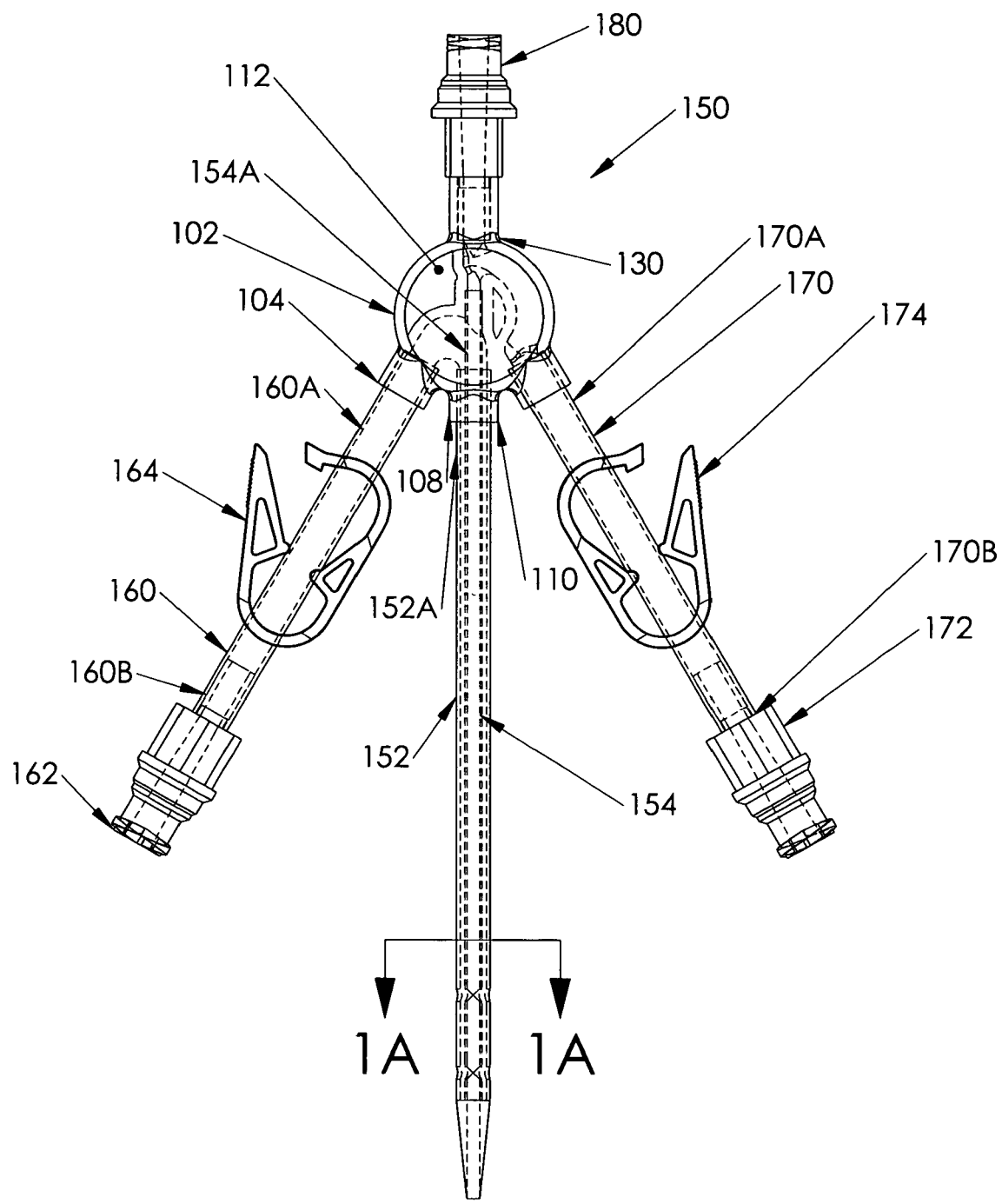
FIG. 1 is a plan view of a catheter utilizing a catheter hub according to a first embodiment of the present invention.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of a catheter in the catheter assembly according to the present invention. The terminology includes the words above specifically mentioned, derivatives thereof, and words of similar import. The following describes preferred embodiments of the invention. However, it should be understood based on this disclosure, that the invention is not limited by the preferred embodiments described herein.

Referring now to the drawings in detail, there is shown in FIG. 1 a catheter assembly indicated generally as 150. The catheter assembly 150 shown in FIG. 1 is a co-axial double lumen assembly, although those skilled in the art will recognize that a single lumen assembly or a catheter assembly with more than two lumens may be used within the spirit and scope of the present invention.

The catheter assembly 150 of the present invention may be adapted for use in various applications in which bodily fluids, medicaments or other solutions are introduced into and removed from the patient's body, such as perfusion, infusion, plasmapheresis, hemodialysis, chemotherapy, and the like. The area to be catheterized is preferably a blood vessel such as an internal jugular vein, but may be any suitable area within the body. Other areas in which the catheter assembly may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 150 may be used to remove or introduce fluids in various areas to be catheterized.

The embodiment of the catheter assembly 150 as shown in FIGS. 1 and 1A is preferably useful for intake, or removal, of blood to be purified from a blood vessel, such as the internal jugular vein, and introduction of purified blood into the same vessel. The blood may be purified by any suitable hemodialysis apparatus (not shown) attached in fluid communication with lumens of the catheter assembly 150 of the invention. The catheter assembly 150 may also be used to introduce medication or other fluids, including, for example, glucose or saline solutions into the patient's body.

For the purposes of describing the preferred embodiments of the present invention, the catheter assembly 150 will be described with respect to the preferred application of hemodialysis, more specifically, for purifying blood flowing through the internal jugular vein. However, it will be understood by one skilled in the art based on this disclosure, that the catheter assembly 150 may be configured and adapted, by increasing or decreasing the catheter size and/or number of catheters and/or lumens in the catheter assembly 150, such that the catheter assembly 150 may be beneficially used for other medical applications in which fluids are introduced into and/or removed from the body.

The catheter assembly 150 incorporates a catheter hub 100 according to the present invention. The catheter hub 100 according to an embodiment of the present invention is shown in detail in FIGS. 2 and 3. The catheter hub 100 includes a hub body 102 and a plurality of ports each shown to comprise an opening or entrance defined within a short collar extending therefrom, within which either the catheter proximal end or extension tube distal ends are affixable to the hub. A first port 104 is fluidly connected through a first conduit 106 to a second port 108. Fluid flowing through the first conduit 106 turns an angle of at least 135 degrees, and preferably approximately 150 degrees between the first port 104 and the second port 108. The second port 108 is associated with the catheter proximal end and includes a first hub cannula 110 fluidly communicating with first conduit 106. A second hub cannula 112 fluidly communicates with the first conduit 106 proximally of the second port 108. As may be seen from FIGS. 2 and 3, the second hub cannula 112 is preferably smaller in diameter than the first hub cannula 110. As may be seen from FIG. 3, the first hub cannula 110 and the second hub cannula 112 are preferably co-axial. Further, while the second hub cannula 112 is shown in FIG. 2 to extend only to the first conduit 106, those skilled in the art will recognize that the second hub cannula 112 may extend into the first conduit 106 toward the second port 108.

A third port 120 fluidly communicates through a second conduit 122 to the second hub cannula 112. Fluid flowing through the second conduit 122 turns an angle of at least 135 degrees, and preferably approximately 150 degrees between the third port 120 and the second hub cannula 112.

A fourth port 130 fluidly communicates with the third port 120 and with the second hub cannula 112. Preferably, the fourth port 130 is aligned with the second hub cannula 112 to form a generally straight line through the second hub cannula 112 between the fourth port 130 and the second port 108. The straight line feature between the fourth port 130 and the second port 108 facilitates insertion of a guidewire (not shown) through the hub 100 during insertion of the catheter assembly 150 into the patient.

Preferably, the catheter hub 100 is constructed from an amorphous polymer, such as polystyrene, polycarbonate, or ABS, although those skilled in the art will recognize that the catheter hub 100 may be constructed from other suitable biocompatible materials. Also preferably, the catheter hub 100 is constructed by molding a top portion 140 of the catheter hub 100, shown in FIG. 3, and a bottom portion 142 of the catheter hub 100, wherein the bottom portion 142 is generally a mirror image of the top portion 140 of the catheter hub 100. The top portion 140 and the bottom portion 142 are joined together along centerline 143. The top portion 140 and the bottom portion 142 may be joined by an adhesive, by solvent bonding, by ultrasonic bonding, or other suitable method known to those skilled in the art. As seen in FIG. 3, the first, second and third ports 104, 108, 120 all lay generally in a plane "P" containing the centerline 143, wherein the plane P extends perpendicularly out of the plane of the paper. Further, the fourth port 130 (not shown in FIG. 3) also generally lies in the plane P.

Optionally, a pair of suture wings 144, shown in FIG. 2 as an example, may extend from the hub body 102. Each suture wing 144 may include a suture opening 146 to enable a physician to suture the catheter hub 100 to the patient's skin so that the catheter hub 100 does not move after the catheter assembly 150 is inserted into the patient. The suture wings 144 are preferably disposed between the first port 104 and the fourth port 130 and between the fourth port 130 and the third port 120, as shown in FIG. 2. It is desired that two suture wings 144 be used to provide even support for the hub 100 after the hub 100 is connected to the patient. While two suture wings 144 are shown in FIG. 2, those skilled in the art will recognize that more or less suture wings may be present without departing from the scope of the invention.

The catheter hub 100 may be used in a version of the catheter assembly 150 that utilizes co-axial lumens, such as the DUO FLOW® catheter, manufactured by Medical Components, Inc. of Harleysville, Pennsylvania. Referring to FIGS. 1 and 1A, an exemplary catheter assembly 150 includes first and second co-axial lumens 152, 154, respectfully, extending distally from the second port 108. A proximal portion 152A of the first lumen 152 fluidly communicates with the first hub cannula 110 and the first port 104. A proximal portion 154A of the second lumen 154 fluidly communicates with the second hub cannula 112, as well as with the third port 120 and the fourth port 130. The proximal portion 154A of the second lumen 154 extends through the first hub cannula 110, but does not fluidly communicate with the first hub cannula 110.

A first extension tube 160 is connected at a distal end 160A to the first port 104 to allow fluid communication between the first extension tube 160 and the first port 104. A proximal end 160B of the first extension tube 160 is connected to a first connector 162, such as a luer lock, as is well known in the art. A catheter clamp 164 is preferably disposed over the first extension tube 160 between the distal end 160A and the proximal end 160B to releasably secure fluid flow between the first connector 162 and the catheter hub 100, as is also well known in the art.

A second extension tube 170 is connected at a distal end 170A to the third port 120 to allow fluid communication between the second extension tube 170 and the third port 120. A proximal end 170B of the second extension tube 170 is connected to a second connector 172, such as a luer lock, as is well known in the art. A catheter clamp 174 is preferably disposed over the second extension tube 170 between the distal end 170A and the proximal end 170B to releasably secure fluid flow between the second connector 172 and the catheter hub 100, as is also well known in the art.

A third connector 180 is preferably fixedly connected to the fourth port 130. The connector 180 is shown in FIG. 1 to be directly connected to the fourth port 130 to minimize the extension length of the third connector 180 away from the hub body 102. However, those skilled in the art will recognize that a conduit, such as an extension tube (not shown), may be disposed between the third connector 180 and the fourth port 130, such that a proximal end of the extension tube is connected to the third connector 180, and a distal end of the extension tube is connected to the fourth port 130. Preferably, the extension tube is extremely flexible so that the extension tube can bend over to move the third connector 180 away from the patient's neck.

Figure 4:
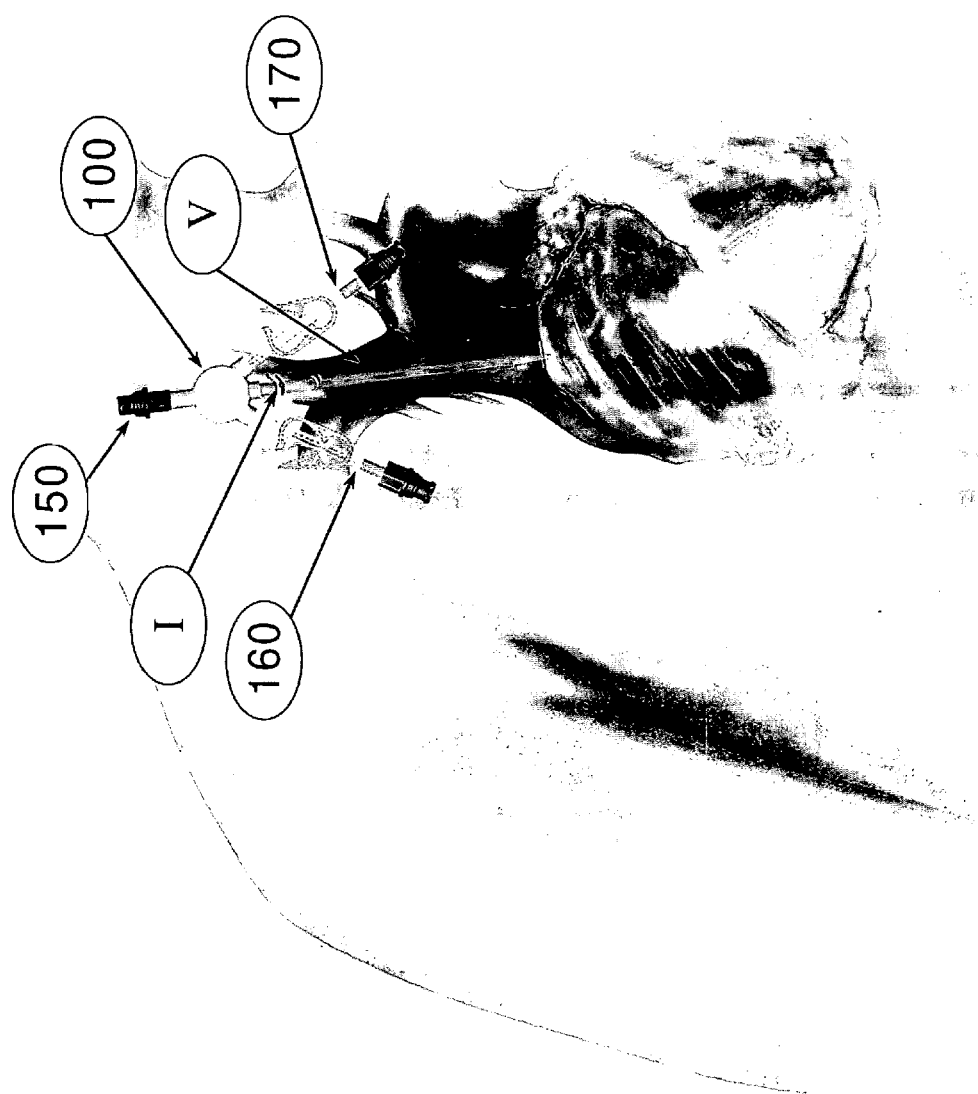
FIG. 4 is a front view of the catheter and catheter hub, according to the first embodiment of the present invention inserted into a patient.

A diagram of the catheter assembly 150 installed through an incision "I" into a patient's jugular vein "V" is shown schematically in FIG. 4. The catheter assembly 150 may be inserted over a catheter guide wire (not shown) during insertion of the catheter assembly 150 into the patient, as is well known in the art, so that, after the catheter assembly 150 is inserted into the patient, the guidewire may be withdrawn from the catheter assembly 150 by pulling the guidewire in a proximal direction from the fourth port 130. As may be seen from FIG. 4, while the catheter hub 100 is disposed proximate to the patient's neck area, the first and second extension tubes 160, 170, respectfully, extend generally downward, away from the patient's neck, so as not to interfere with the patient as he/she turns his/her head. The third connector 180 interferes minimally with the patient.

Referring to the catheter assembly of FIG. 1, in use, the first and second extension tubes 160, 170 are hooked up to a medical device, such as a hemodialysis machine (not shown), as is well known in the art. Blood is withdrawn from the patient through the first lumen 152, through the first cannula 110, through the first conduit 106 and the first port 104, and through the first extension tube 160 to the hemodialysis machine. Processed blood is returned from the machine to the patient through the second extension tube 170, the third port 120, and the second conduit 122 to the second hub cannula 112, and then through the second hub cannula 112 and the second lumen 154 to the patient.

If it is desired to administer additional fluids to the patient, such as, for example, medication, the medication may be administered by connecting a device, such as a syringe (not shown), to the hub 100 at the third connector 180. The syringe is inserted through the fourth port 130 and into the second hub cannula 112, so that the additional fluids may be administered directly into the second lumen 154 and into the patient.

Figure 5A:
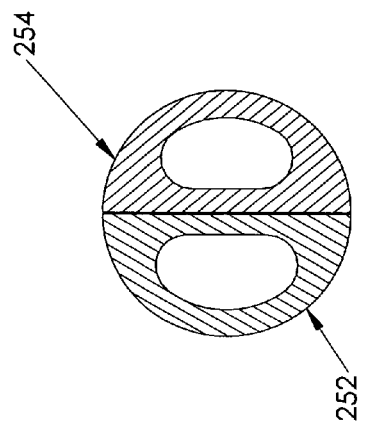
FIG. 5A is an enlarged sectional view of the catheter taken along lines 5A-5A of FIG. 5.
Figure 5:
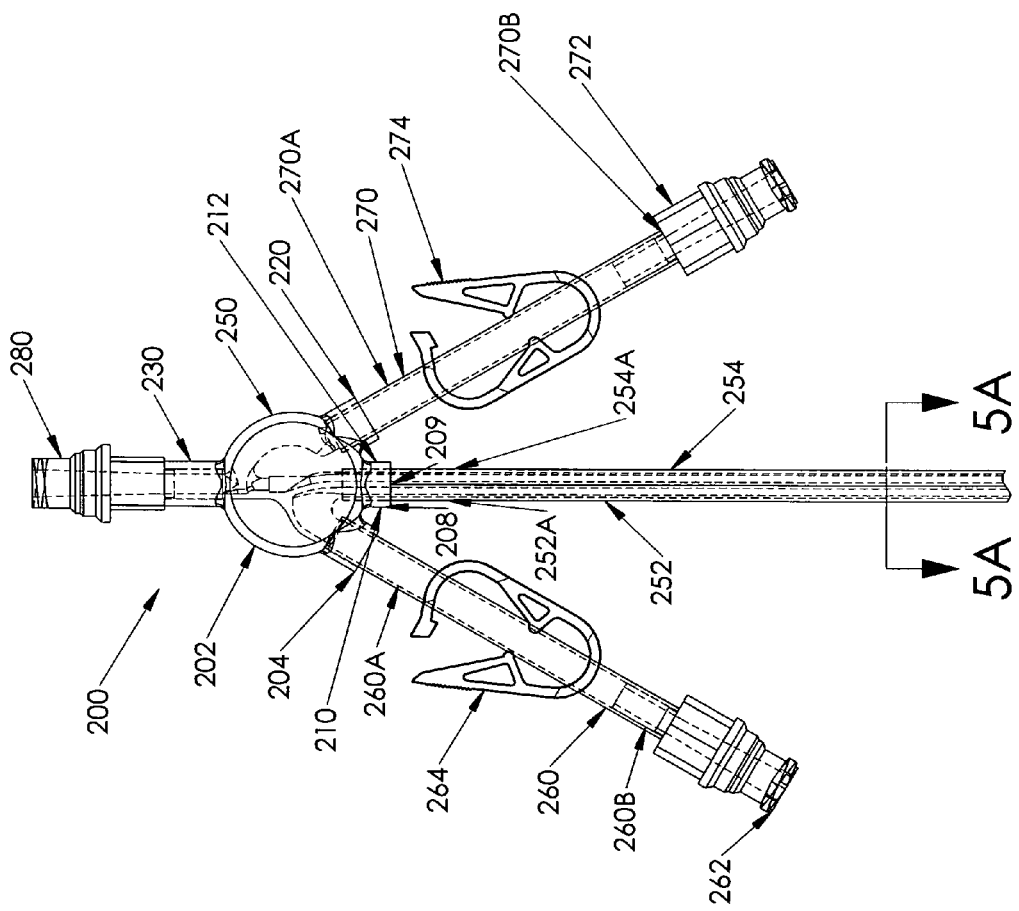
FIG. 5 is a plan view of a catheter utilizing a catheter hub according to a second embodiment of the present invention.
Figure 6:
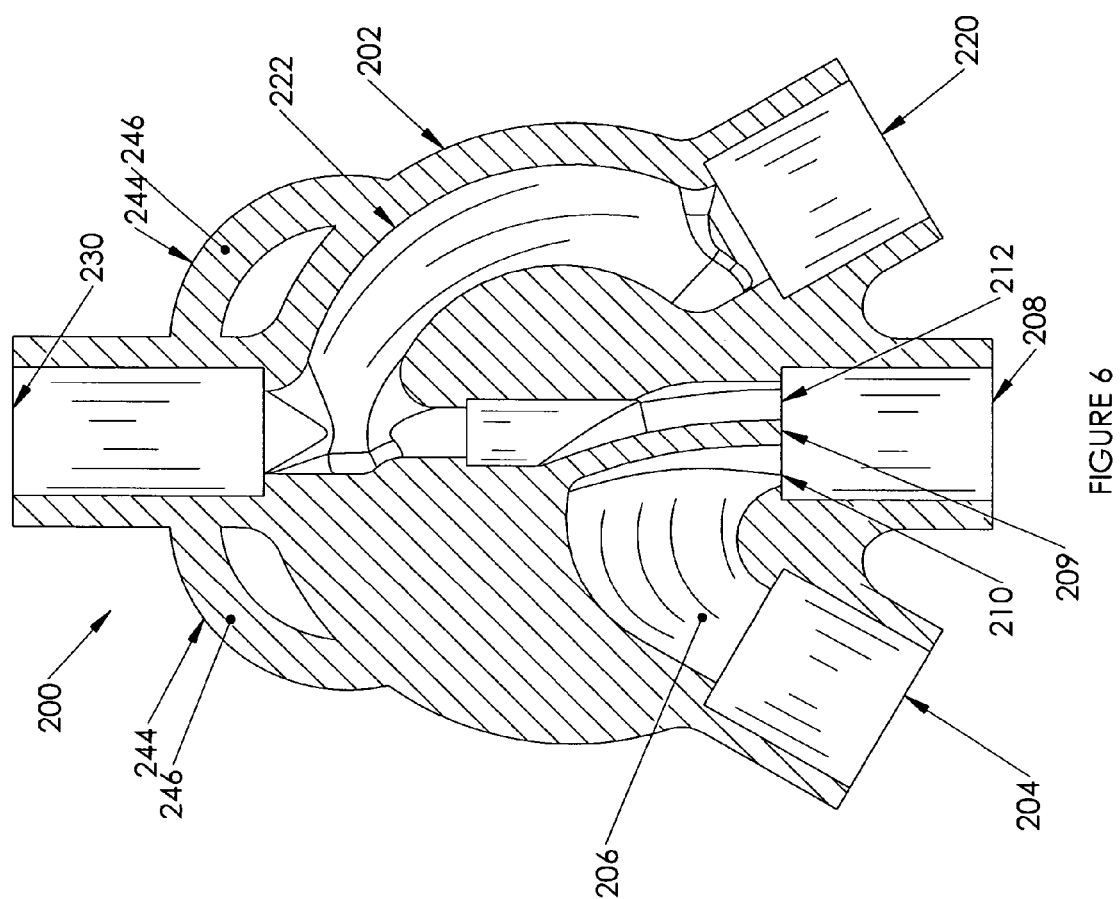
FIG. 6 is an enlarged plan view, in section, of the catheter hub according to the second embodiment of the present invention.

A catheter assembly 250 that employs an alternate embodiment of a catheter hub 200 according to the present invention is shown in FIGS. 5, 5A and 6. The catheter assembly utilizes side-by-side lumens 252, 254. An example of a catheter assembly that may utilize the catheter hub 200 is the SPLIT-CATH® catheter, manufactured by Medical Components, Inc. of Harleysville, Pa.

Figure 7:
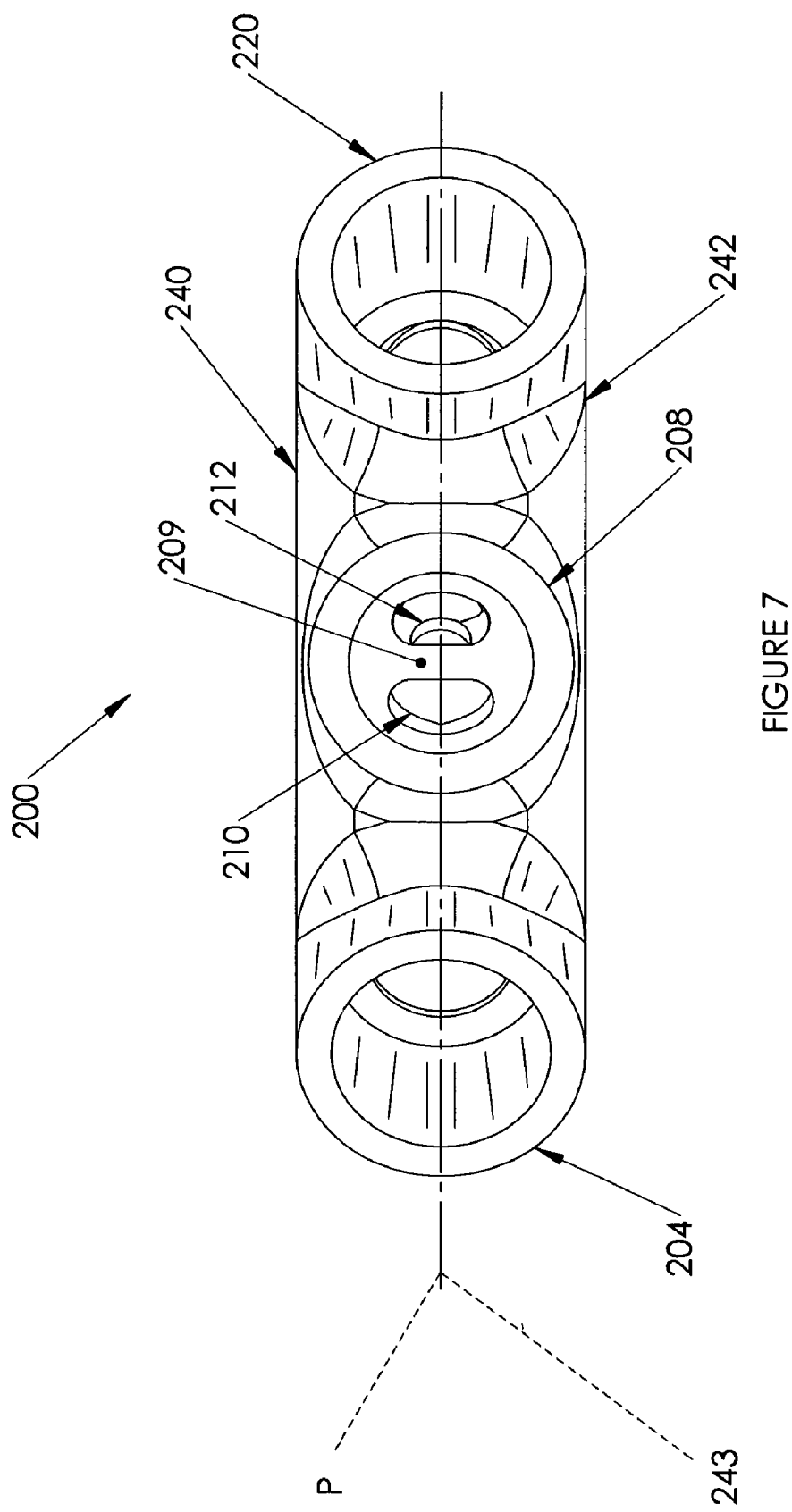
FIG. 7 is an enlarged side view of the catheter hub according to the second embodiment of the present invention.

Referring now to FIGS. 6-7, the hub 200 includes a hub body 202 and a plurality of ports extending therefrom. A first port 204 is fluidly connected through a first conduit 206 to a second port 208. The second port 208 is divided by a septum 209 into a first hub cannula 210 and a second hub cannula 212. The first port 204 fluidly communicates only with the first hub cannula 210. The first conduit 206 turns an angle of at least 135 degrees, and preferably approximately 150 degrees between the first port 204 and the second port 208.

A third port 220 is fluidly connected through a second conduit 222 to the second port 208. The third port 220 fluidly communicates only with the second hub cannula 212. The second conduit 222 turns an angle of at least 135 degrees, and preferably approximately 150 degrees between the first third port 220 and the second port 208. The second hub cannula 212 provides fluid communication between the second conduit 222 and the second port 208.

A fourth port 230 fluidly communicates with the third port 220 and to the second hub cannula 212. Preferably, the fourth port 230 is aligned with the second hub cannula 212 to form a generally straight line through the second hub cannula 212 between the fourth port 230 and the second port 208. The straight line feature between the fourth port 230 and the second port 208 facilitates insertion of a guidewire (not shown) through the hub 200 during insertion of the catheter assembly 250 into the patient.

Preferably, the catheter hub 200 is constructed from an amorphous polymer, such as polystyrene, polycarbonate, or ABS, although those skilled in the art will recognize that the catheter hub 200 may be constructed from other suitable biocompatible materials. Also preferably, the catheter hub 200 is constructed by molding a top portion 240 of the catheter hub 200, shown in FIG. 7, and a bottom portion 242 of the catheter hub 200, wherein the bottom portion 242 is generally a mirror image of the top portion 240 of the catheter hub 200. The top portion 240 and the bottom portion 242 are joined together along centerline 243. The top portion 240 and the bottom portion 242 may be joined by an adhesive, by solvent bonding, by ultrasonic bonding, or other suitable method known to those skilled in the art. As seen in FIG. 7, the first, second and third ports 204, 208, 220 all lay generally in a plane "P", containing the centerline 243, wherein the plane P extends perpendicularly out of the plane of the paper. Further, the fourth port 230 (not shown in FIG. 7) also generally lies in the plane P.

Optionally, a pair of suture wings 244, shown only in FIG. 6 as an example, may extend from the hub body 202. The suture wings 244 may each include a suture opening 246 to enable a physician to suture the catheter hub 200 to the patient's skin so that the catheter hub 200 does not move while the catheter assembly 250 is inserted into the patient. The suture wings 244 are preferably disposed between the first port 204 and the fourth port 230 and between the fourth port 230 and the third port 220, as shown in FIG. 6. While two suture wings 244 are shown in FIG. 6, those skilled in the art will recognize that more or less suture wings may be present without departing from the scope of the invention.

Referring to FIGS. 5 and 5A, the catheter assembly 250 includes first and second lumens 252, 254, respectfully, extending distally from the second port 208. A proximal portion 252A of the first lumen 252 fluidly communicates with the first hub cannula 210 but does not fluidly communicate with the second hub cannula 212. A proximal portion 254A of the second lumen 254 fluidly communicates with the second hub cannula 212 but does not fluidly communicate with the first hub cannula 210.

Referring still to FIG. 5, a first extension tube 260 is connected at a distal end 260A to the first port 204 to allow fluid communication between the first extension tube 260 and the first port 204. A proximal end 260B of the first extension tube 260 is connected to a first connector 262, such as a luer lock, as is well known in the art. A catheter clamp 264 is preferably disposed over the first extension tube 260 between the distal end 260A and the proximal end 260B to releasably secure fluid flow between the first connector 262 and the catheter hub 200, as is also well known in the art.

A second extension tube 270 is connected at a distal end 270A to the third port 220 to allow fluid communication between the second extension tube 270 and the third port 220. A proximal end 270B of the second extension tube 270 is connected to a second connector 272, such as a luer lock, as is well known in the art. A catheter clamp 274 is preferably disposed over the second extension tube 270 between the distal end 270A and the proximal end 270B to releasably secure fluid flow between the second connector 272 and the catheter hub 200, as is also well known in the art.

A third connector 280 is preferably fixedly connected to the fourth port 230. The connector 280 is shown in FIG. 5 to be directly connected to the fourth port 230 to minimize the extension length of the third connector 280 away from the hub body 202. However, those skilled in the art will recognize that a conduit, such as an extension tube (not shown), may be disposed between the third connector 280 and the fourth port 230, such that a proximal end of the extension tube is connected to the third connector 280, and a distal end of the extension tube is connected to the fourth port 230.

The catheter assembly 250 is inserted into the patient in generally the same manner as the catheter assembly 150 is inserted into the patient as shown in FIG. 4. The operation of the catheter assembly 250 is similar to the operation of the catheter assembly 150 as described above. However, instead of fluid being withdrawn from and returned to the patient by co-axial lumens 152, 154, the fluid is withdrawn from and returned to the patient by adjacent lumens 252, 254, respectively.

A catheter assembly 350 that employs a third embodiment of a catheter hub 300 according to the present invention is shown in FIGS. 8-11. The catheter assembly 350 utilizes triple lumens connected to the catheter hub 300, and is shown in detail in FIGS. 8A and 11.

Figure 8:
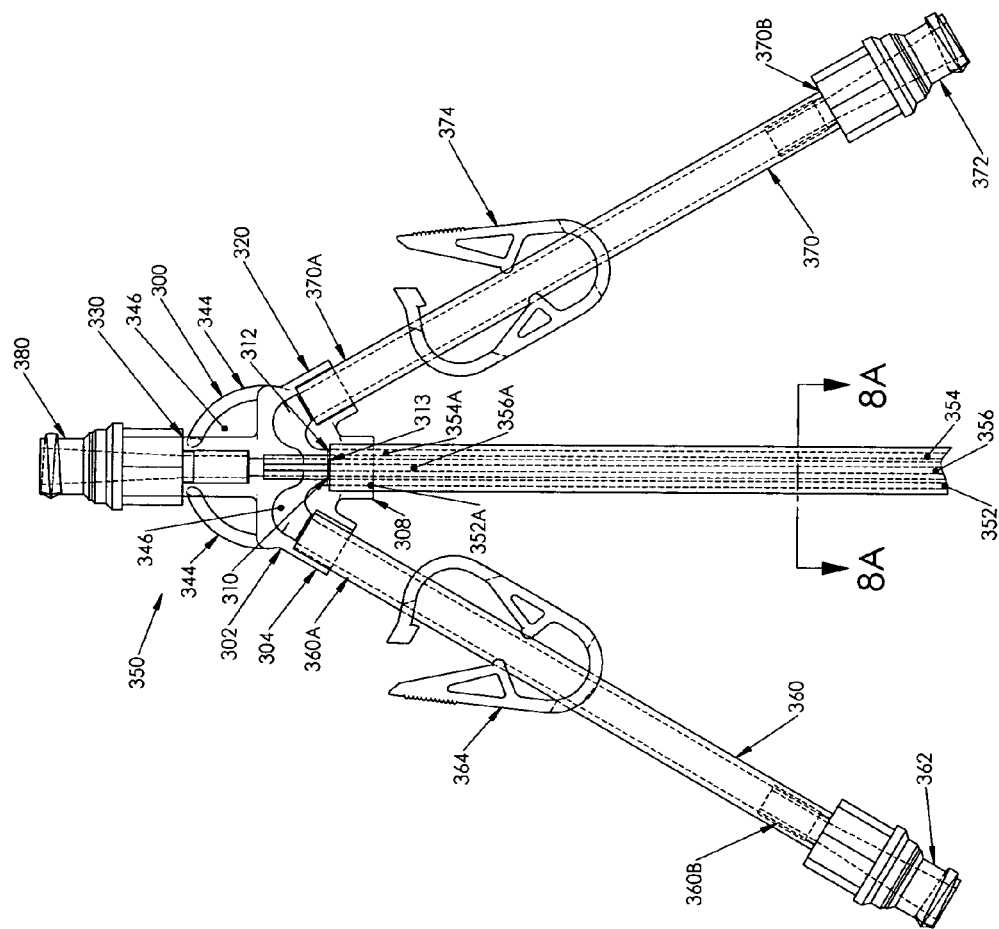
FIG. 8 is a plan view of a catheter utilizing a catheter hub according to a third embodiment of the present invention.
Figure 8A:
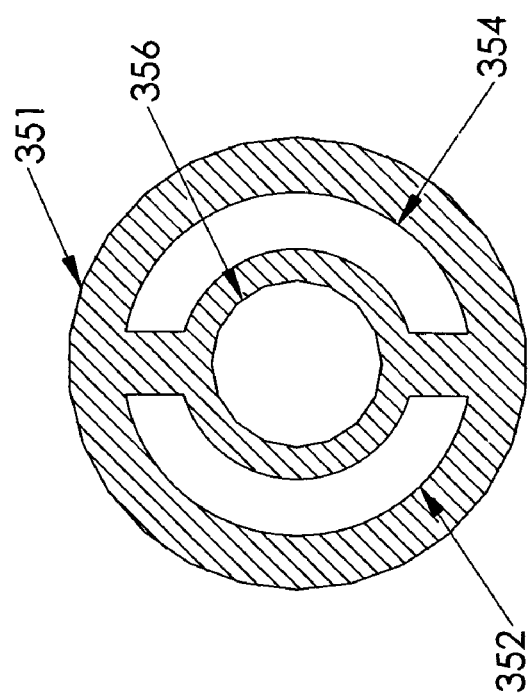
FIG. 8A is an enlarged sectional view of the catheter taken along lines 8A-8A of FIG. 8.
Figure 9:
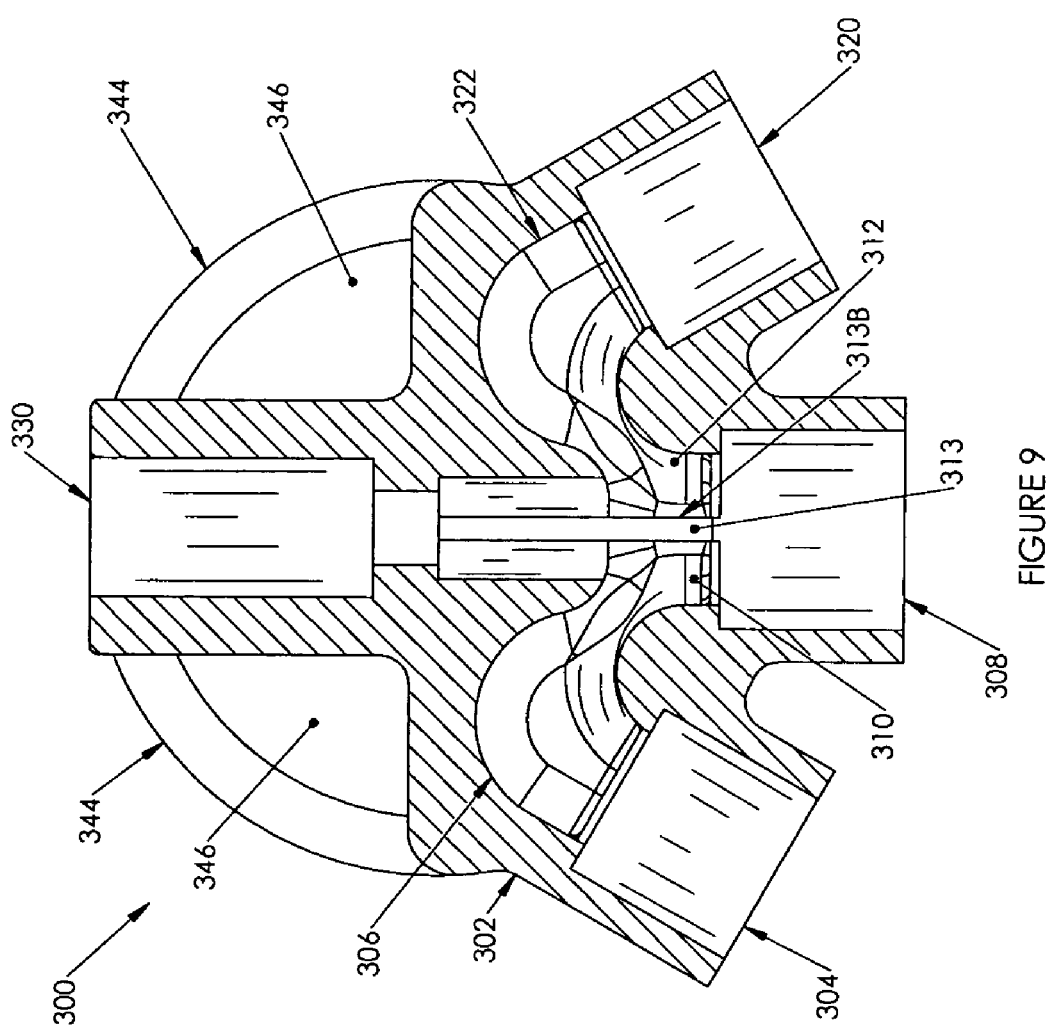
FIG. 9 is an enlarged plan view, in section, of the catheter hub according to the third embodiment of the present invention.
Figure 10:
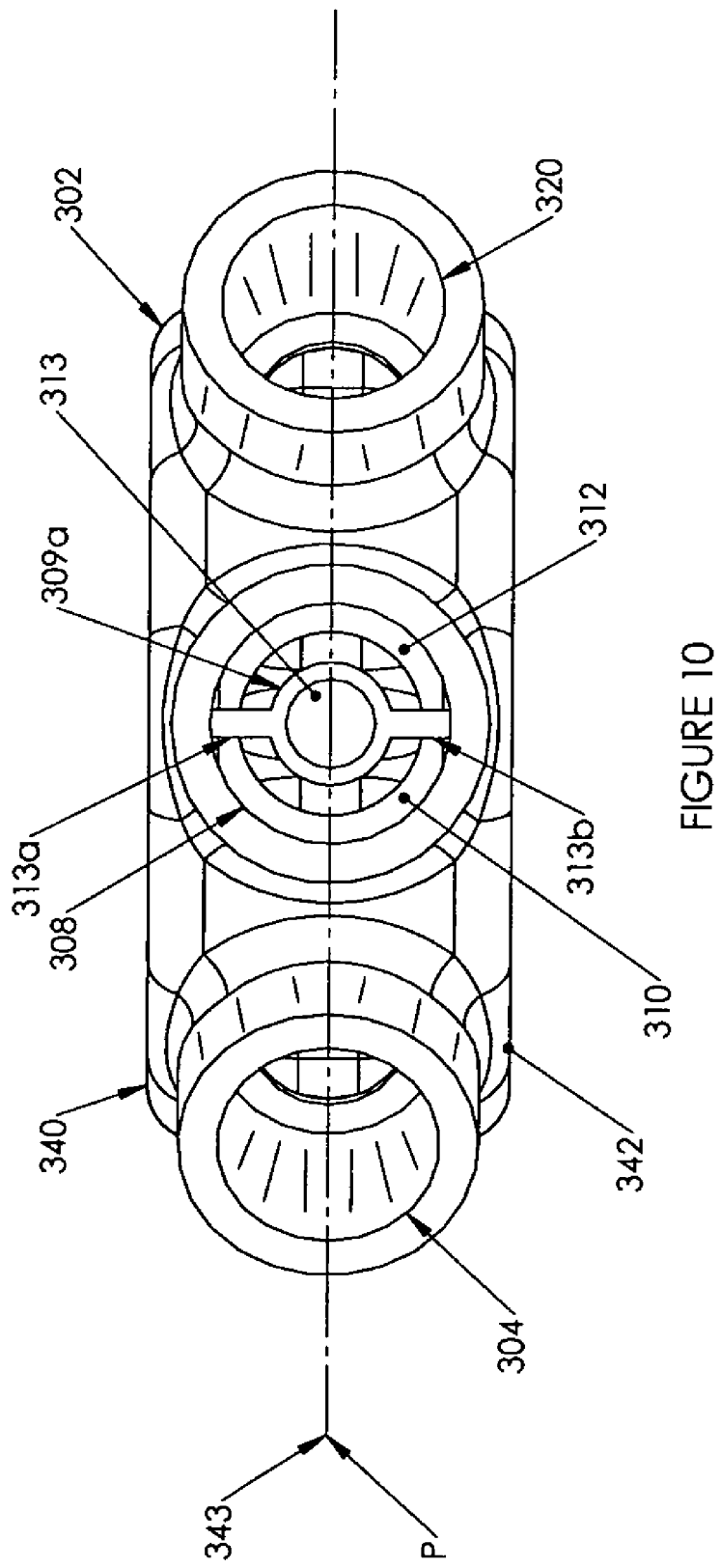
FIG. 10 is an enlarged side view of the catheter hub according to the third embodiment of the present invention.

Referring to FIGS. 8-10, the hub 300 includes a hub body 302 and a plurality of ports extending therefrom. A first port 304 is fluidly connected through a first conduit 306 to a second port 308. The second port 308 is divided into a first hub cannula 310, a second hub cannula 312, and a third hub cannula 313. The third hub cannula 313 includes an upper slot 313a and a lower slot 313b that each extend between the second port 308 and the fourth port 330. The upper and lower slots 313a, 313b are disposed to engage a catheter 351 (shown in FIGS. 8A and 11) connected to the hub 300. The first port 304 fluidly communicates only with the first hub cannula 310 in the second port 308. The first conduit 306 turns an angle of at least 135 degrees, and preferably approximately 150 degrees between the first port 304 and the second port 308.

A third port 320 is fluidly connected through a second conduit 322 only with the second hub cannula 312 to the second port 308. The second conduit 322 turns an angle of at least 135 degrees, and preferably approximately 150 degrees between the third port 320 and the second port 308.

A fourth port 330 fluidly communicates with the third hub cannula 313. Preferably, the fourth port 330 is aligned with the third hub cannula 313 to form a generally straight line through the third hub cannula 313 between the fourth port 330 and the second port 308. The straight line feature between the fourth port 330 and the second port 308 facilitates insertion of a guidewire (not shown) through the hub 300 during insertion of the catheter assembly 350 into the patient.

Preferably, the catheter hub 300 is constructed from an amorphous polymer, such as polystyrene, polycarbonate, or ABS, although those skilled in the art will recognize that the catheter hub 300 may be constructed from other suitable biocompatible materials. Also preferably, the catheter hub 300 is constructed by molding a top portion 340 of the catheter hub 300, shown in FIG. 10, and a bottom portion 342 of the catheter hub 300, wherein the bottom portion 342 is generally a mirror image of the top portion 340 of the catheter hub 300. The top portion 340 and the bottom portion 342 are joined together along centerline 343. As seen in FIG. 10, the first, second and third ports 304, 308, 320 all lay generally in a plane "P" containing the centerline 343, wherein the plane P extends perpendicularly out of the plane of the paper. Further, the fourth port 330 (not shown in FIG. 10) also generally lies in the plane P.

Optionally, suture wings 344, shown in FIGS. 8 and 9 as an example, may extend from the hub body 302. Each suture wing 344 may include a suture opening 346 to enable a physician to suture the catheter hub 300 to the patient's skin so that the catheter hub 300 does not move while the catheter assembly 350 is inserted into the patient. As shown in FIG. 9, the suture wing 344 may be disposed between first port 304 and the fourth port 330, and also between the fourth port 330 and the third port 320.

Referring back to FIGS. 8 and 8A, the catheter assembly 350 includes a catheter 351 having first, second, and third lumens 352, 354, 356, respectfully, extending distally from the second port 308.

Figure 11:
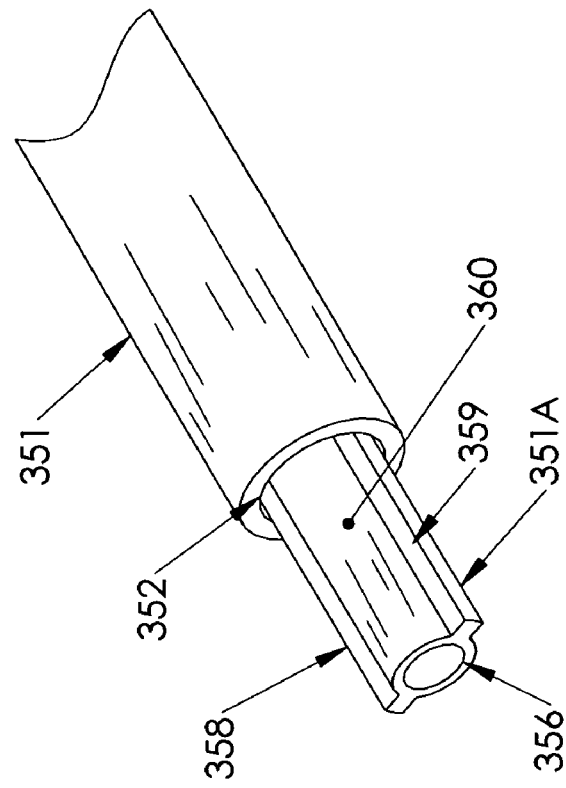
FIG. 11 is a perspective view of a proximal end of a catheter adapted to be inserted into the catheter hub according to the third embodiment of the present invention.

A proximal end 351A of the catheter 351 is shown in FIG. 11. The proximal end 351A of the catheter 351 includes first and second septums 358, 359 that, along with the third lumen 356, separate the first lumen 352 from the second lumen 354. The first septum 358 is inserted in the upper slot 313a and the second septum 359 is inserted into the lower slot 313b so that first, second, and third hub cannulae 310, 312, 313 are fluidly separated from each other.

Referring back to FIG. 8, a proximal portion 352A of the first lumen 352 fluidly communicates with the first hub cannula 310 but does not fluidly communicate with the second or third hub cannulae 312, 313. A proximal portion 354A of the second lumen 354 fluidly communicates with the second hub cannula 312 but does not fluidly communicate with the first or third hub cannulae 310, 313. A proximal portion 356A of the third lumen 356 fluidly communicates with the third hub cannula 313 but does not fluidly communicate with the first or second hub cannulae 310, 312. Preferably, third lumen 356 has a generally circular cross section, with each of the first and second lumens 352, 354 having generally semi-annular cross-sections disposed about the lumen 356 as shown in the cross-sectional view of the lumens 352, 354, 356 is shown in FIG. 8A.

Referring back to FIG. 8, a first extension tube 360 is connected at a distal end 360A to the first port 304 to allow fluid communication between the first extension tube 360 and the first port 304. A proximal end 360B of the first extension tube 360 is connected to a first connector 362, such as a luer lock, as is well known in the art. A catheter clamp 364 is preferably disposed over the first extension tube 360 between the distal end 360A and the proximal end 360B to releasably secure fluid flow between the first connector 362 and the catheter hub 300, as is also well known in the art.

A second extension tube 370 is connected at a distal end 370A to the third port 320 to allow fluid communication between the second extension tube 370 and the third port 320. A proximal end 370B of the second extension tube 370 is connected to a second connector 372, such as a luer lock, as is well known in the art. A catheter clamp 374 is preferably disposed over the second extension tube 370 between the distal end 370A and the proximal end 370B to releasably secure fluid flow between the second connector 372 and the catheter hub 300, as is also well known in the art.

A third connector 380 is preferably fixedly connected to the fourth port 330. The connector 380 is shown in FIG. 8 to be directly connected to the fourth port 330 to minimize the extension length of the third connector 380 away from the hub body 302. However, those skilled in the art will recognize that a conduit, such as an extension tube (not shown), may be disposed between the third connector 380 and the fourth port 330, such that a proximal end of the extension tube is connected to the third connector 380, and a distal end of the extension tube is connected to the fourth port 330.

The catheter assembly 350 is inserted into the patient in generally the same manner as the catheter assembly 150 is inserted into the patient as shown in FIG. 4. The operation of the catheter assembly 350 is similar to the operation of the catheter assembly 150 as described above, with the exception that, with three separate lumens 352, 354, 356 in the catheter assembly 350, instead of the two separate co-axial lumens 152, 154 in the catheter assembly 150, the catheter assembly 350 may be used to circulate fluid, such as blood, in a patient during a procedure, such as hemodialysis using the first and second lumens 352, 354, while the third lumen 356 may be used to administer additional fluid, such as a medicament, during the procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter hub for a catheter to be implanted, for securing extension tube assemblies to a proximal end thereof for fluid communication with respective lumens of the catheter, comprising:
a generally annular body having:
a first port;
a second port at which the catheter hub is connectable to the catheter proximal end, the second port fluidly communicating with the first port through a first conduit, wherein fluid flowing into the first conduit from the first port turns within the annular body at an angle of greater than approximately 135 degrees between the first port and the second port;
a third port fluidly communicating with the second port through a second conduit, wherein fluid flowing into the second conduit from the third port turns within the annular body at an angle of greater than approximately 135 degrees between the third port and the second port; and
a fourth port fluidly communicating with the second port, wherein the fourth port and the second port are generally co-axial,
wherein the first, second, third and fourth ports have respective lengths just sufficient to enable connection thereof to respective ends of the catheter and extension tube assemblies, whereby the body may be compact in size.

2. The catheter hub according to claim 1, wherein fluid flowing into the first conduit from the first port turns within the annular body at an angle of approximately 150 degrees.

3. The catheter hub according to claim 1, wherein fluid flowing into the second conduit from the third port turns within the annular body at an angle of approximately 150 degrees.

4. The catheter hub according to claim 1, wherein the second port comprises a first portion and a second portion; wherein the first port fluidly communicates with the first portion; and wherein the third and fourth ports fluidly communicate with the second portion.

5. The catheter hub according to claim 1, wherein the second port comprises a first portion, a second portion, and a third portion; wherein the first port fluidly communicates with the first portion; wherein the third port fluidly communicates with the second portion; and wherein the fourth port fluidly communicates with the third portion.

6. The catheter hub according to claim 1, wherein the second port includes entrances to a plurality of conduits that transmit fluid in different directions, whereby the second port is adapted to transmit fluid in a plurality of directions.

7. The catheter hub according to claim 6, wherein the second port is adapted to simultaneously transmit fluid in a plurality of directions.

8. A catheter assembly comprising:
a hub having a generally annular body having:
a first port;
a second port fluidly communicating with the first port through a first conduit, wherein fluid flowing into the first conduit from the first port turns within the annular body at an angle of greater than approximately 135 degrees between the first port and the second port;
a third port fluidly communicating with the second port through a second conduit, wherein fluid flowing into the second conduit from the third port turns within the annular body at an angle of greater than approximately 135 degrees between the third port and the second port; and
a fourth port fluidly communicating with the second port, wherein the fourth port and the second port are generally co-axial; and
a catheter having a proximal end connected to the hub at the second port and having a first lumen fluidly communicating with the second port and to the first port; and further having a second lumen fluidly connected through the second port to the third port and the fourth port,
wherein the first, second, third and fourth ports have respective lengths just sufficient to enable connection thereof to respective ends of the catheter and extension tube assemblies, whereby the body may be compact in size.

9. The catheter assembly according to claim 8, wherein the first lumen and the second lumen are co-axial.

10. The catheter assembly according to claim 8, wherein the first lumen and the second lumen are adjacent to each other.

11. The catheter assembly according to claim 8, wherein fluid flowing into the first conduit from the first port turns within the annular body at an angle of approximately 150 degrees.

12. The catheter assembly according to claim 8, wherein fluid flowing into the second conduit from the third port turns within the annular body at an angle of approximately 150 degrees.

13. The catheter assembly according to claim 8, wherein the second port is adapted to transmit fluid in a plurality of directions.

14. The catheter assembly according to claim 13, wherein the second port is adapted to simultaneously transmit fluid in a plurality of directions.

15. A catheter hub for a catheter to be implanted, for securing extension tube assemblies to a proximal end thereof for fluid communication with respective lumens of the catheter, comprising:
a generally annular hub body having:
a first port extending from the hub body;
a second port at which the catheter hub is connectable to the catheter proximal end, the second port extending from the hub body, wherein the second port fluidly communicates with the first port through a first conduit, and wherein fluid flowing into the first conduit from the first port turns within the annular body at an angle of greater than approximately 135 degrees between the first port and the second port;
a third port extending from the hub body, wherein the third port fluidly communicates with the second port through a second conduit, and wherein fluid flowing into the second conduit from the third port turns within the annular body at an angle of greater than approximately 135 degrees between the third port and the second port; and
a fourth port extending from the hub body, wherein the fourth port fluidly communicates with the second port, and wherein the fourth port and the second port are generally co-axial,
wherein the first port, the second port, the third port, and the fourth port all lie in a plane defined by the hub body, and
wherein the first, second, third and fourth ports have respective lengths just sufficient to enable connection thereof to respective ends of the catheter and extension tube assemblies, whereby the body may be compact in size.

16. The catheter hub according to claim 15, wherein fluid flowing into the first conduit from the first port turns within the annular body at an angle of approximately 150 degrees.

17. The catheter hub according to claim 15, wherein fluid flowing into the second conduit from the third port turns within the annular body at an angle of approximately 150 degrees.

18. The catheter hub according to claim 15, wherein the second port comprises a first portion and a second portion; wherein the first port fluidly communicates with the first portion; and wherein the third and fourth ports are fluidly communicating with the second portion.

19. The catheter hub according to claim 15, wherein the second port comprises a first portion, a second portion, and a third portion; wherein the first port fluidly communicates with the first portion; wherein the third port fluidly communicates with the second portion; and wherein the fourth port fluidly communicates with the third portion.

20. The catheter hub according to claim 15, wherein the second port includes entrances to a plurality of conduits that transmit fluid in different directions, whereby the second port is adapted to transmit fluid in a plurality of directions.

21. The catheter hub according to claim 20, wherein the second port is adapted to simultaneously transmit fluid in a plurality of directions.

22. A catheter hub for a catheter to be implanted, for securing extension tube assemblies to a proximal end thereof for fluid communication with respective lumens of the catheter, comprising:
a generally annular body having:
a first port;
a second port at which the catheter hub is connectable to the catheter proximal end, the second port fluidly communicating with the first port through a first conduit, wherein fluid flowing into the first conduit from the first port turns within the annular body at an angle of greater than approximately 135 degrees between the first port and the second port; and
a third port fluidly communicating with the second port through a second conduit, wherein fluid flowing into the second conduit from the third port turns within the annular body at an angle of greater than approximately 135 degrees between the third port and the second port,
wherein the first, second, and third ports have respective lengths just sufficient to enable connection thereof to respective ends of the catheter and extension tube assemblies, whereby the body may be compact in size.

23. The catheter hub according to claim 22, further comprising a fourth port fluidly communicating with at least one of the first port, the second port, and the third port.

24. The catheter hub according to claim 23, wherein the fourth port fluidly communicates with the second port.

25. The catheter hub according to claim 22, wherein at least one of the first, second and third ports comprises an opening defined by a short collar extending from the hub within which either the catheter or an extension tube is affixable to the hub.

26. The catheter assembly according to claim 1, wherein at least one of the first, second, third and fourth ports comprises an opening defined by a short collar extending from the hub within which either the catheter or an extension tube is affixable to the hub.

27. The catheter hub according to claim 8, wherein at least one of the first, second, third and fourth ports comprises an opening defined by a short collar extending from the hub within which either the catheter or an extension tube is affixable to the hub.

28. The catheter hub according to claim 15, wherein at least one of the first, second, third and fourth ports comprises an opening defined by a short collar extending from the hub body within which either the catheter or an extension tube is affixable to the hub.

* * * * *